United States Patent
Eherts et al.

(10) Patent No.: US 6,261,847 B1
(45) Date of Patent: Jul. 17, 2001

(54) SAMPLE DILUTION MODULE WITH OFFSET MIXING CHAMBER

(75) Inventors: Robert W. Eherts, Middletown; Evandro S. Denunzio, Scarsdale, both of NY (US)

(73) Assignee: Bayer Corporation, Tarrytown, NY (US)

( * ) Notice: Subject to any disclaimer, the term of this patent is extended or adjusted under 35 U.S.C. 154(b) by 0 days.

(21) Appl. No.: 09/113,464

(22) Filed: Jul. 10, 1998

(51) Int. Cl.$^7$ .......................................................... B01L 3/02
(52) U.S. Cl. .............................. 436/179; 436/52; 436/53; 436/174; 436/180; 73/864.11; 73/864.12; 422/81; 422/82; 422/100
(58) Field of Search ..................................... 436/174, 179, 436/180, 52, 53; 422/99, 100, 81, 82; 73/863.71, 864.01, 864.11, 864.12, 864.13, 864.14

(56) References Cited

U.S. PATENT DOCUMENTS

| | | |
|---|---|---|
| 1,547,562 | 7/1925 | Byrd . |
| 2,104,325 | 1/1938 | Juffa . |
| 2,398,737 | 4/1946 | Elliot et al. . |
| 2,538,695 * | 1/1951 | Mathis . |
| 2,595,493 | 5/1952 | Slaby et al. . |
| 2,697,945 | 12/1954 | Dovas . |
| 2,737,812 | 3/1956 | Haak . |
| 2,836,979 | 6/1958 | Ryley . |
| 3,039,500 * | 6/1962 | Goldberg . |
| 4,007,639 | 2/1977 | Haeckel . |
| 4,014,652 | 3/1977 | Ishibashi et al. . |
| 4,418,041 | 11/1983 | Johnson et al. . |
| 5,000,921 | 3/1991 | Hanaway et al. . |
| 5,045,286 | 9/1991 | Kitajima et al. . |
| 5,133,218 | 7/1992 | Uffenhiemer et al. . |
| 5,159,842 | 11/1992 | Palmer . |
| 5,183,765 | 2/1993 | Qureshi et al. . |
| 5,195,657 * | 3/1993 | Wells . |
| 5,218,875 | 6/1993 | Volpe et al. . |
| 5,268,147 * | 12/1993 | Zabetakis et al. . |
| 5,399,497 * | 3/1995 | Kumar et al. . |
| 5,773,305 | 6/1998 | Zabetakis et al. . |
| 5,785,926 * | 7/1998 | Seubert et al. . |

FOREIGN PATENT DOCUMENTS

| | | |
|---|---|---|
| 0 562 260 A2 | 9/1993 | (EP) . |
| 1 226 584 | 3/1972 | (GB) . |
| 1 316 982 | 5/1973 | (GB) . |

* cited by examiner

*Primary Examiner*—Jan Ludlow
(74) *Attorney, Agent, or Firm*—Andrew L. Klawitter, Esq.; Rodman & Rodman

(57) ABSTRACT

The sample dilution module includes an oil filled aspiration probe and mixing chamber that communicate with each other while the mixing chamber is maintained at an angle of approximately 5 to 45 degrees below a horizontal axis. The aspiration probe is maintained in a vertical orientation. A micro-bubble is aspirated between separate aspirations of test sample and diluent to prevent contact between the sample and diluent in the aspiration probe. The test sample and diluent are then drawn from the vertically oriented aspiration probe into the mixing chamber. After the sample and diluent are in the mixing chamber the micro-bubble of air can migrate away from the test sample and diluent to enable the test sample and diluent to contact each other. Mixing of the test sample and diluent is accomplished by moving the test sample and diluent back and forth in the mixing chamber without physical agitation of the mixing chamber and without any mixing element in the mixing chamber. Such movement is accomplished by alternate suction and vacuum forces imposed on the fluid in the mixing chamber.

16 Claims, 7 Drawing Sheets

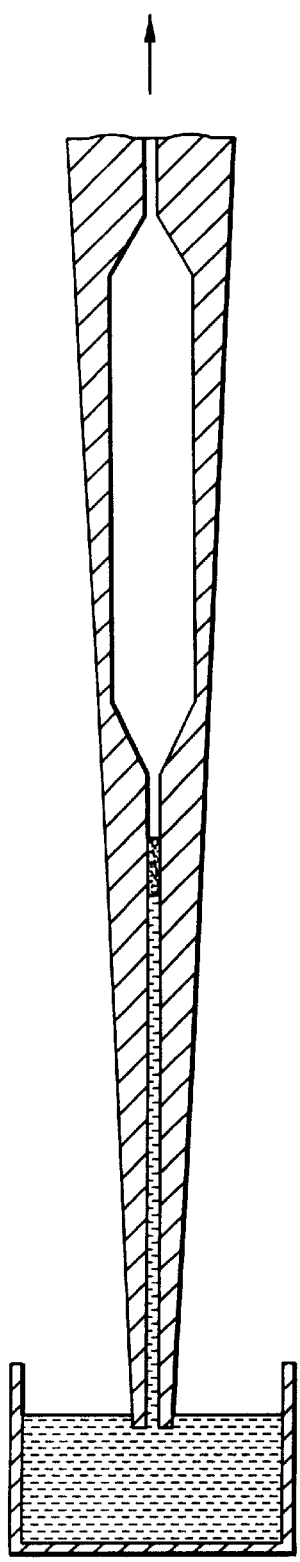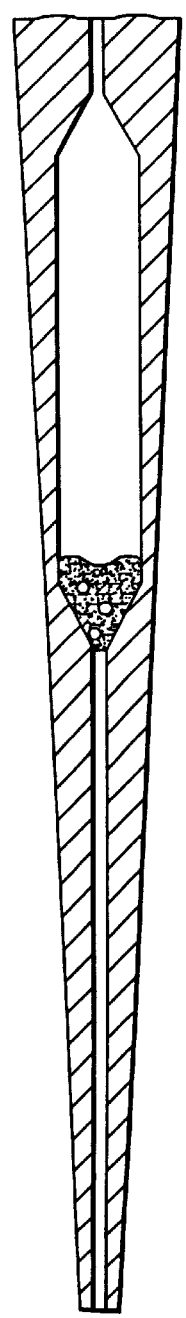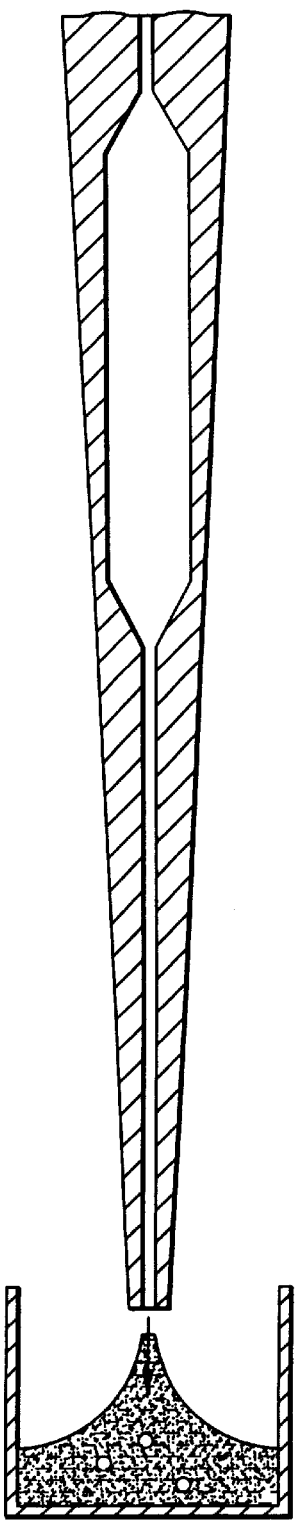
FIG.1
PRIOR ART
FIG.2
PRIOR ART
FIG.3
PRIOR ART

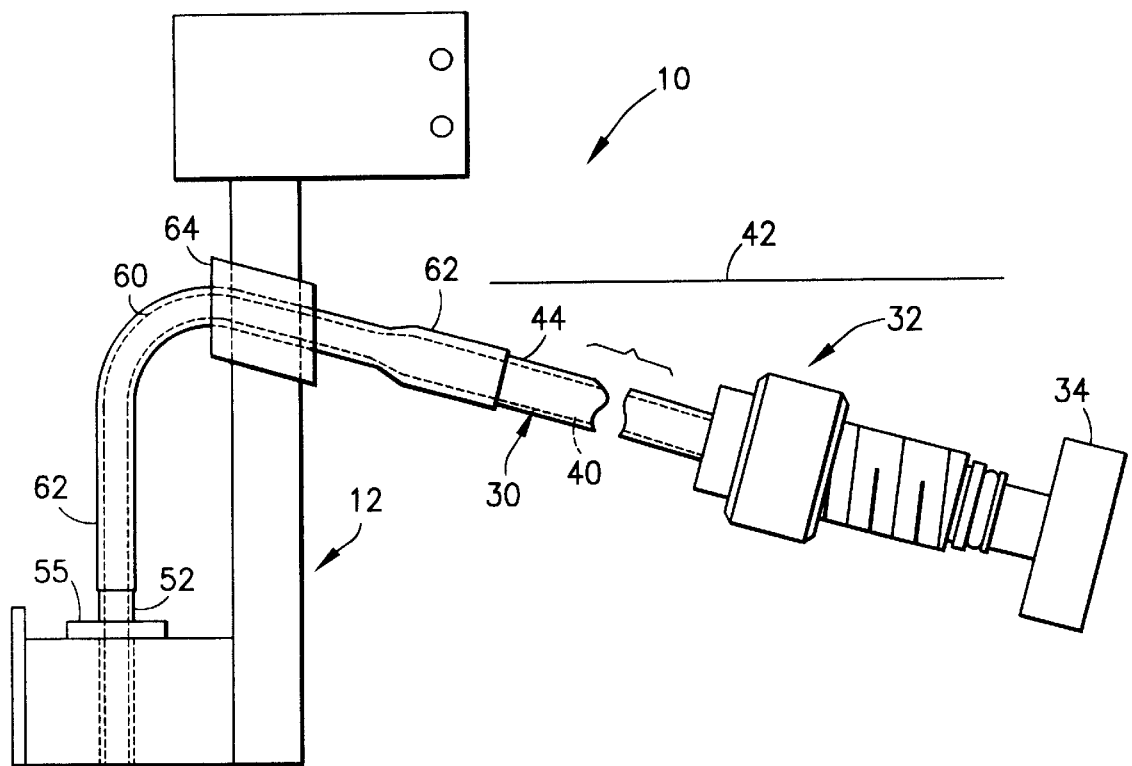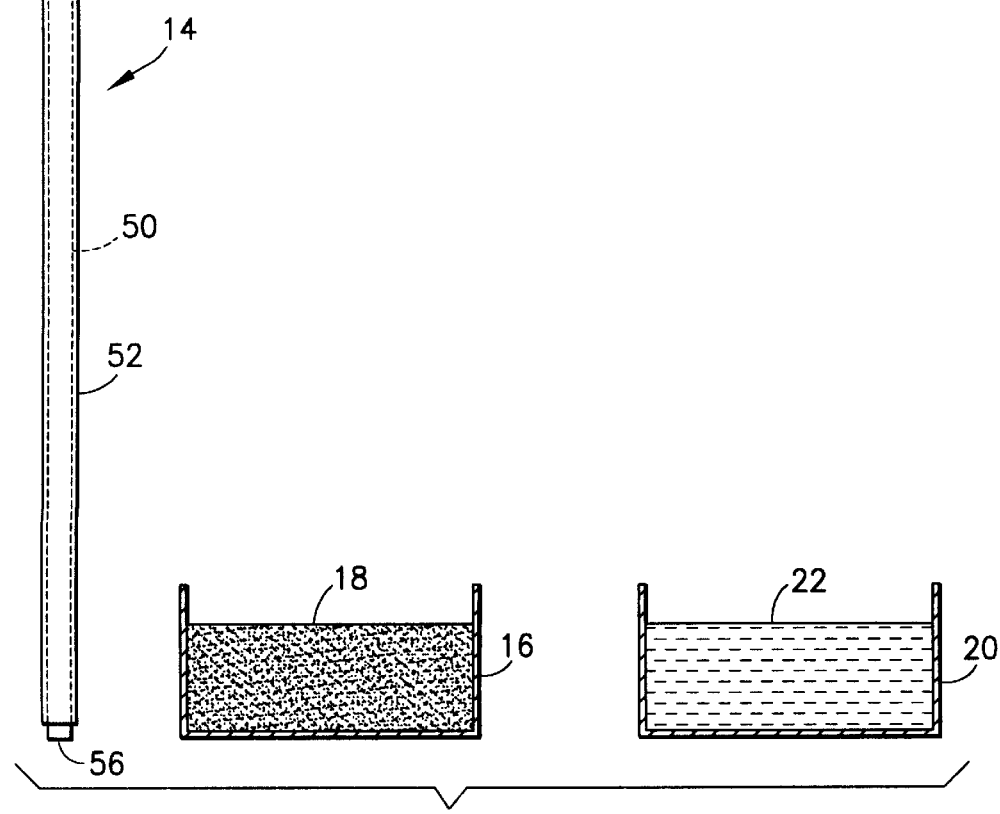
FIG.4

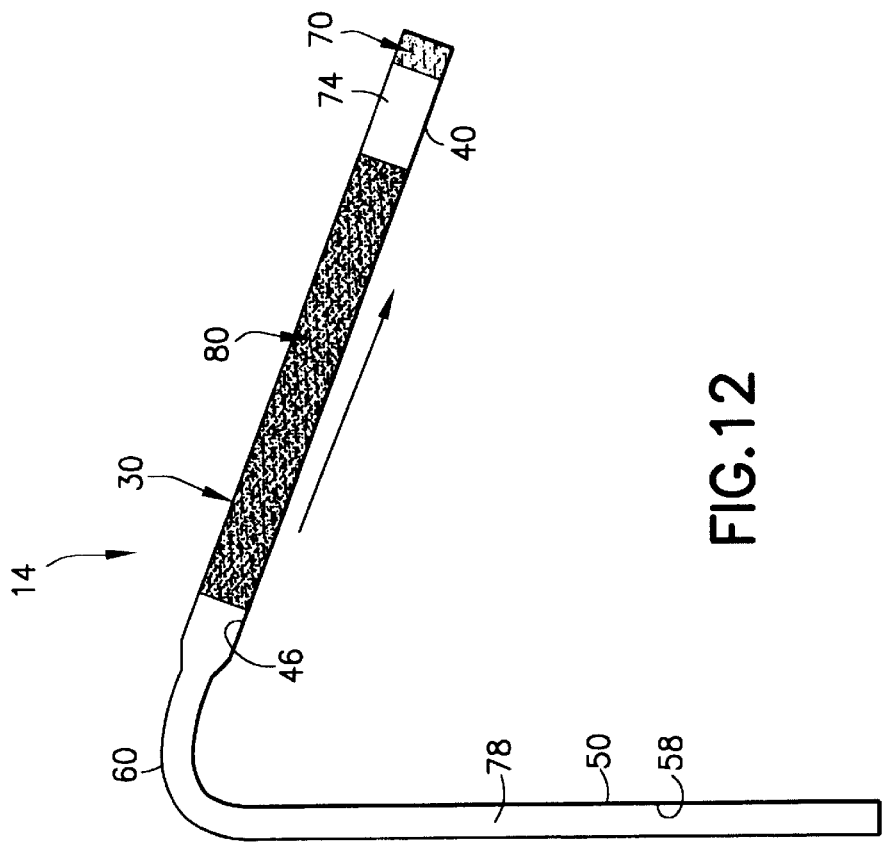
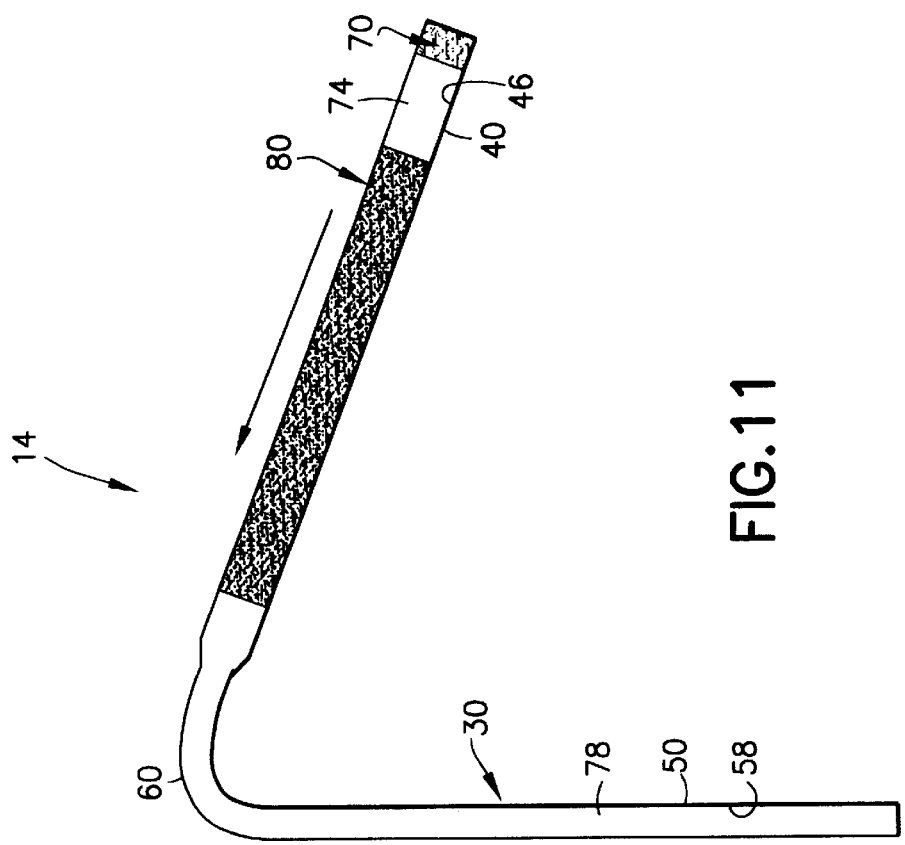

SAMPLE DILUTION MODULE WITH OFFSET MIXING CHAMBER

BACKGROUND OF THE INVENTION

This invention relates to the preparation of test samples for automatic analysis in a sample analysis system and more particularly to a novel apparatus and method for diluting a test sample before it is combined with a reagent in a sample analysis system.

In known automatic sampling systems, such as shown in U.S. Pat. No. 5,268,147, test samples of blood or serum are permitted to react with one or more reagents to produce measurable test results that are the basis for an analytical determination of blood characteristics. Known sampling systems often include a pipette or sampling probe to aspirate a predetermined volume of test sample from a container such as a tube or cuvette. The aspirated test sample is usually mixed with a predetermined volume of diluent before the test sample is added to a reagent. Dilution of the test sample helps control a test reaction when the test sample is combined with a reagent.

One known system for diluting a fluid sample, indicated as prior art in FIGS. 1–3, includes an aspiration probe with two continuous communicable interior sections of different diametrical magnitude. A first interior section of the aspiration probe is proximate an inlet opening, and a second interior section of larger diametrical magnitude is located beyond the first section. Both interior sections of the probe are generally disposed along a vertical axis.

Predetermined amounts of fluid sample and diluent are sequentially aspirated into the first interior section, as detailed in U.S. Pat. No. 5,773,305. The fluid sample and diluent are then drawn further into the probe from the first interior section to the second interior section.

The fluid sample and diluent, when located in the second interior section, are moved back and forth along a substantially vertical axis a predetermined number of times by alternate vacuum and pressure forces. Repeated back and forth movement of the fluid sample and diluent in the second interior section of the probe provides substantially uniform mixing or dilution of the fluid sample.

In many instances an oil coating is provided along the inside surface of the probe and the mixing chamber to facilitate flow and reduce carryover of sample or diluent to a next use of the device. Applicants have found that an oil filled aspiration line and mixing chamber wherein the oil can be withdrawn in the hydraulic line by a pump and later reintroduced into the hydraulic line during dispensation of a diluted test sample serves to minimize carryover.

It is thus desirable to provide a method and apparatus for diluting a test sample and diluent which minimizes carryover of sample or diluent to a next use of an aspiration device.

OBJECTS AND SUMMARY OF THE INVENTION

Among the several objects of the invention may be noted the provision of a novel method and apparatus for diluting a test sample, a novel method and apparatus for diluting a test sample wherein a selected amount of test sample and a selected amount of diluent are aspirated and mixed together in an aspiration line, a novel method and apparatus for diluting a test sample that is separated from diluent by an air bubble which does not result in inclusion of the air bubble in the diluted test sample, a novel method and apparatus for mixing test sample with diluent that permits use of an oil filled line prior to sample aspiration and during dispensation of a diluted test sample.

Other objects and features of the invention will be in part apparent and in part pointed out hereinafter.

In accordance with the invention the sample dilution module includes an aspiration probe for separately aspirating a first predetermined amount of test sample from a test sample container and a second predetermined amount of diluent from a diluent container. The aspiration probe has an inlet opening and an aspiration path extending from the inlet opening along a substantially vertical axis.

A mixing section is joined to the aspiration probe and has a mixing chamber communicable with the aspiration path of the aspiration probe. The mixing chamber is inclined approximately 5 to 45 degrees below the horizontal axis, preferably 15 degrees below the horizontal axis. The mixing chamber is without any mixing element and is of a greater diameter than the diameter of the aspiration path. In a preferred embodiment of the invention the mixing section and the aspiration probe are formed as a one-piece structure.

The mixing section communicates with pumping means for drawing the test sample and diluent from the vertical aspiration path in the aspiration probe to the mixing chamber. The pumping means can also alternately exert suction and pressure forces on the test sample and diluent in the mixing chamber to move the test sample and diluent back and forth in the mixing chamber. Such movement is accomplished without agitation of the mixing chamber and provides substantially uniform mixing of the test sample and the diluent thereby resulting in a diluted test sample.

The method of diluting the test sample for analysis in a sample analysis system includes aspirating, in sequence, selected predetermined amounts of test sample and diluent, moving the aspirated test sample and diluent back and forth along an axis that is inclined to the horizontal approximately 5 to 45 degrees. The method further includes separating the aspirated test sample and diluent with an air bubble. Separation of test sample and diluent is accomplished by aspirating the air bubble after aspirating one of the test sample and diluent and then aspirating the other of the test sample and diluent after the air bubble is aspirated.

The method further includes providing a mixing chamber with a volume that is at least two times greater than the volume of the aspirated test sample and diluent. This arrangement enables the air bubble that separates the test sample and diluent to migrate away from the test sample and diluent when the test sample and diluent are moved back and forth in the mixing chamber. The method also includes filling the hydraulic line with oil before aspiration of test sample, drawing the oil into a pump during aspiration of sample and diluent and reversing the movement of the oil toward the opening of the aspiration probe during dispensation of the mixed or diluted test sample from the aspiration probe.

The invention accordingly comprises the method and apparatus hereinafter described, the scope of the invention being indicated in the claims.

DESCRIPTION OF THE DRAWINGS

In the accompanying drawings,

FIGS. 1–3 are simplified schematic sectional views of a prior art system for diluting a test sample;

FIG. 4 is a simplified schematic view of a sample dilution module incorporating one embodiment of the present invention;

FIG. 11 is a view similar to FIG. 10, and in sequence with FIG. 10 showing the aspirated test sample and diluent being moved back and forth in the mixing section;

FIG. 12 is a view similar to FIG. 11, and in sequence with FIG. 11, showing reverse movement of the aspirated test sample and diluent in the mixing section of the probe; and, FIG. 13 is a view similar to FIG. 12, and in sequence with FIG. 12, showing the diluted or mixed test sample being dispensed from the aspiration probe.

Corresponding reference characters indicate corresponding parts throughout the several views of the drawings.

DETAILED DESCRIPTION OF THE INVENTION

Figure 6:
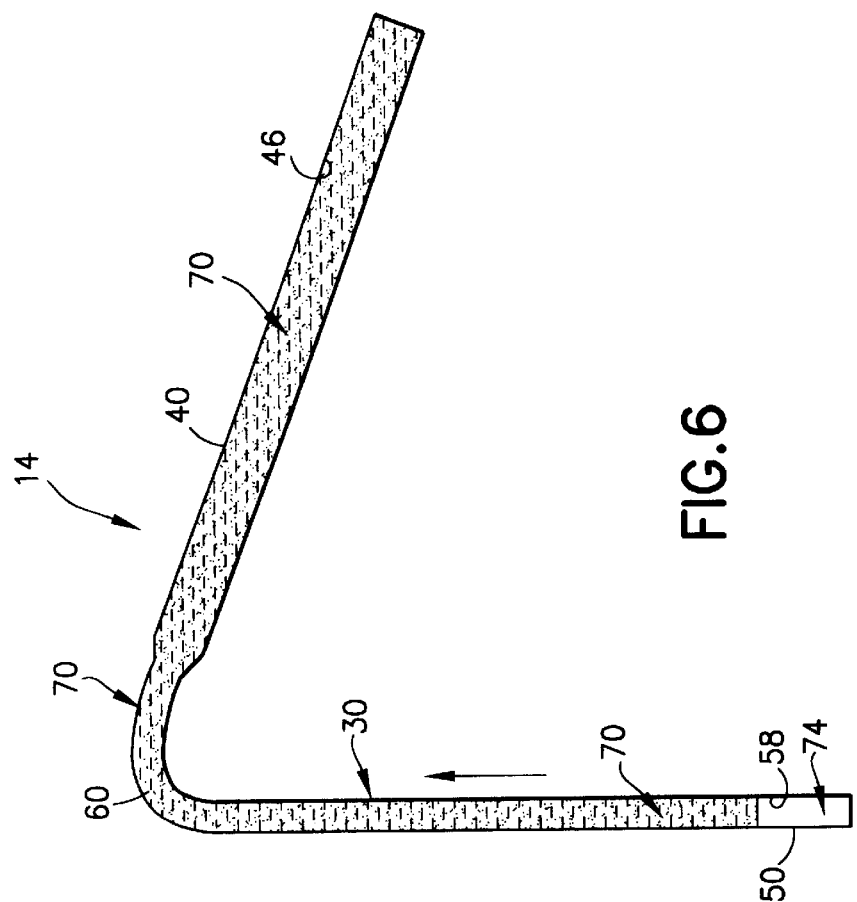
FIG. 6 is a view similar to FIG. 5, and in sequence with FIG. 5, after the probe has aspirated air.

A sample dilution module incorporating one embodiment of the invention is generally indicated by the reference number 10 in FIG. 4.

Referring to FIG. 4 the sample dilution module 10 includes a known probe support 12 for moving a probe assembly 14 into and out of selected fluid containers such as a sample container 16 containing a fluid sample 18 and a diluent container 20 containing diluent 22.

The probe assembly 14 includes a hydraulic line 30 formed of a perfluoropolymer material such as a Teflon with an inner diameter of approximately 1.57 millimeters and an outer diameter of approximately 2.1 millimeters. A suitable known fitting assembly 32 is provided at one end of the hydraulic line 30 for connection with a pump 34 such as a suitable known syringe pump. The pump 34 draws fluid into the hydraulic line 30 during aspiration, provides back and forth movement of fluids within the hydraulic line 30 during mixing, and moves fluid toward and outwardly of the line 30 during aspiration.

The hydraulic line 30 includes an inclined mixing section 40 that has an angle of inclination in the range of approximately 5 to 45 degrees below a horizontal axis 42. Preferably the mixing section 40 has an angle of inclination of approximately 15 degrees below the horizontal axis 42. A plastic outer tubing 44, which can be formed of any suitable plastic material such as perfluoropolymer material is provided around the mixing section 40 to provide stiffness and protection to the mixing section 40.

The hydraulic line 30 is drawn down in a suitable known manner to form a probe section 50 having an internal diameter of approximately 0.60 millimeters and an outside diameter of approximately 1.0 millimeters. The probe section 50 extends along a substantially vertical axis within a metallic sleeve 52 that has a flange 55 which can be formed of stainless steel for purposes of liquid level sensing. The sleeve 52 and the probe section 50 are supported on the probe support 12 in a known manner at the flange 55.

A curved section 60 of the hydraulic line 30 joins the probe section 50 to the mixing section 40. A suitable known heat shrink tubing 62 extends from slightly above the flange 55 to the mixing section 40 to maintain the curvature of the curved section 60. A known orientation clip 64 is provided at an end portion of the mixing section 40 to join the mixing section 40 the probe support 12.

The draw down of the hydraulic line 30 and the disposition of the probe section 50 in the metallic sleeve 52 can be accomplished in the manner disclosed in U.S. Pat. No. 5,639,426.

Although the length and diameter of the probe section 50, the curved section 60 and the mixing section 40 are a matter of choice and the dimensions provided thus far are exemplary, some further exemplary dimensions are a vertical length of approximately 110 millimeters from an open end 56 (FIG. 4) of the probe section 50 to the flange 55, a length of approximately 315 millimeters of the mixing section 40 from the orientation clip 64 to the fitting assembly 32. The open end 56 of the probe section 50, which functions as an inlet and outlet opening, extends slightly below the sleeve 52 for aspiration and dispensation of fluid. The curved section 60 can have a length of approximately 30 millimeters, an internal diameter of approximately 0.60 millimeters and an outside diameter of approximately 1.0 millimeters. The bend radius of the curved section 60 is approximately 9 millimeters. Under this arrangement the sample and diluent are aspirated in amounts that will enable the total sample and diluent to occupy the full cross sectional area of the mixing chamber 40.

Figure 5:
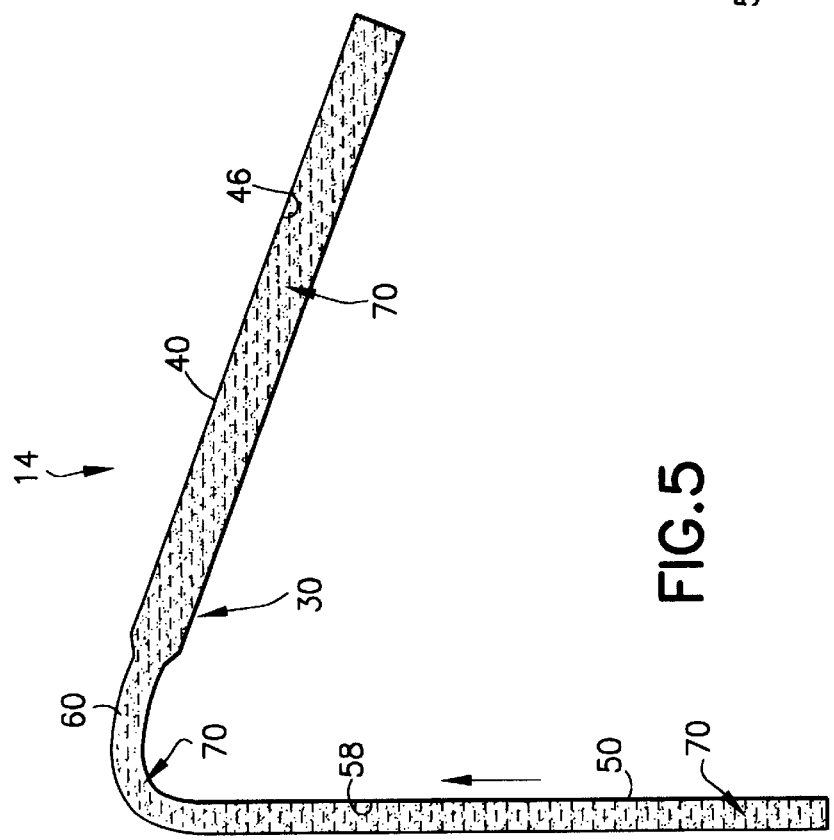
FIG. 5 is a simplified schematic view of the probe and the mixing chamber thereof, after the probe has aspirated hydraulic fluid.

Referring to FIG. 5 the inside surface of the probe section 50 defines a substantially vertical aspiration path 58 and the inside surface of the mixing section 40 defines a mixing chamber 46 that is communicable with the vertical aspiration path 58 through the inside space 66 of the curved section 60.

Referring to FIG. 4 the pumping device 34 provides aspiration suction within the probe section 50, the curved section 60 and the mixing section 40, as desired, to aspirate fluid inside the probe 50. The pumping device 34 also provides a pressure force at the mixing section 40, the curved section 60 and the probe section 50 when it is desired to dispense fluid from inlet/outlet opening 56 of the probe 50 or move fluid toward the opening 56.

In carrying out the method of the present invention, the pump 34, the probe 50, the curved section 60 and the mixing section 40 are filled with a known fluorocarbon oil 70 (FIG. 5), which serves as a hydraulic fluid and a line conditioner. The hydraulic fluid 70 fills the sections 50, 60 and 40 as schematically shown in FIG. 5.

Referring to FIG. 6 the probe 50 aspirates a predetermined amount of air 74 to separate the column of oil 70 from a forthcoming aspiration of the test sample 18.

Figure 7:
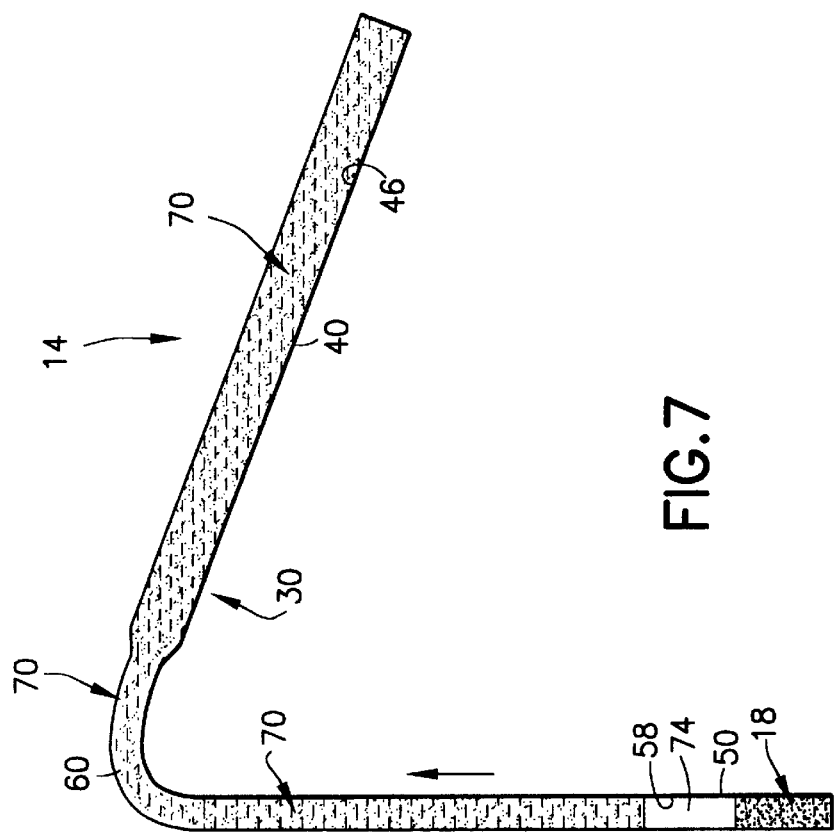
FIG. 7 is a view similar to FIG. 6, and in sequence with FIG. 6, after the probe has aspirated a test sample.

Referring to FIG. 7, the probe 50 aspirates a predetermined volume of test sample 18 from the container 16 such as approximately 1 to 99 microliters. It should be noted that the probe 50 can be selectively positioned in a known manner by the probe support 12 to enter the respective containers from which the desired aspirations are to be made.

Figure 8:
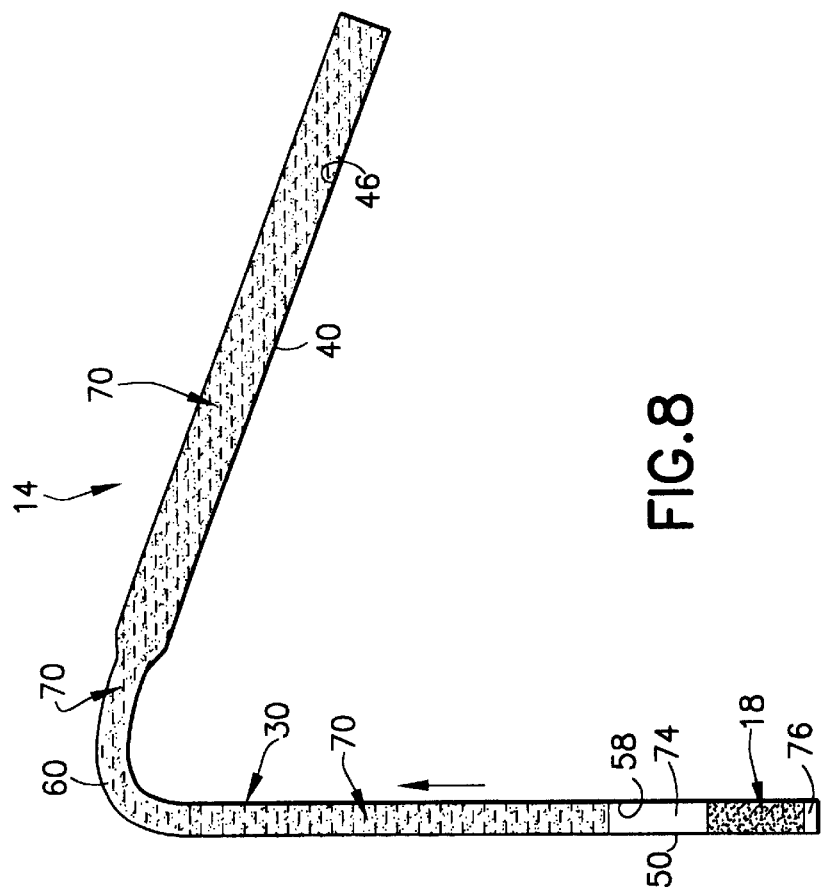
FIG. 8 is a view similar to FIG. 7, and in sequence with FIG. 7, after the probe has aspirated a micro-bubble of air.

Referring to FIG. 8 the probe 50 aspirates a relatively small air segment or air bubble 76 approximately 0.25 to 1 microliters, for example, which urges the previously aspirated test sample 18 inside the probe tip. The air bubble 76 also prevents premature mixing, prevents loss of test sample during probe motion after the test sample is aspirated, prevents loss of test sample into the diluent while the probe is in the diluent vessel 20 (FIG. 4) and thus prevents test sample contamination of diluent in the diluent vessel 20.

Figure 9:
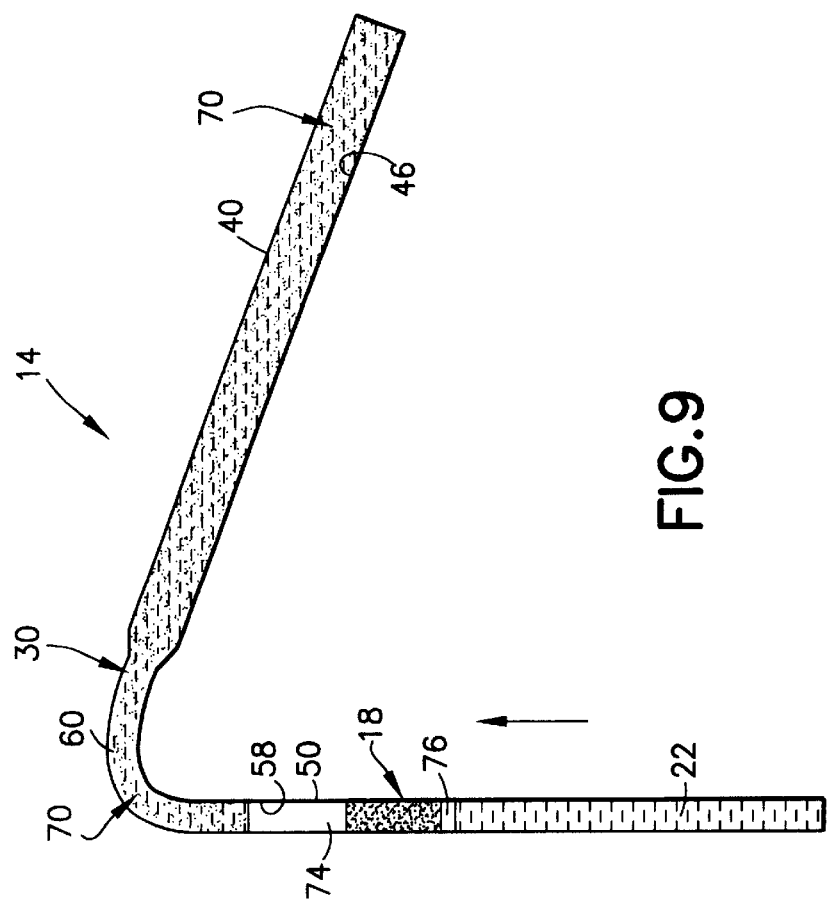
FIG. 9 is a view similar to FIG. 8, and in sequence with FIG. 8, after the probe has aspirated diluent.

Referring to FIG. 9 the probe 50 then aspirates diluent 22 from the container 20, which diluent 22 will eventually be mixed with the previously aspirated test sample 18. If the total desired volume of sample and diluent is 100 microliters the amount of diluent aspirated will be based on the amount of test sample aspirated.

Figure 10:
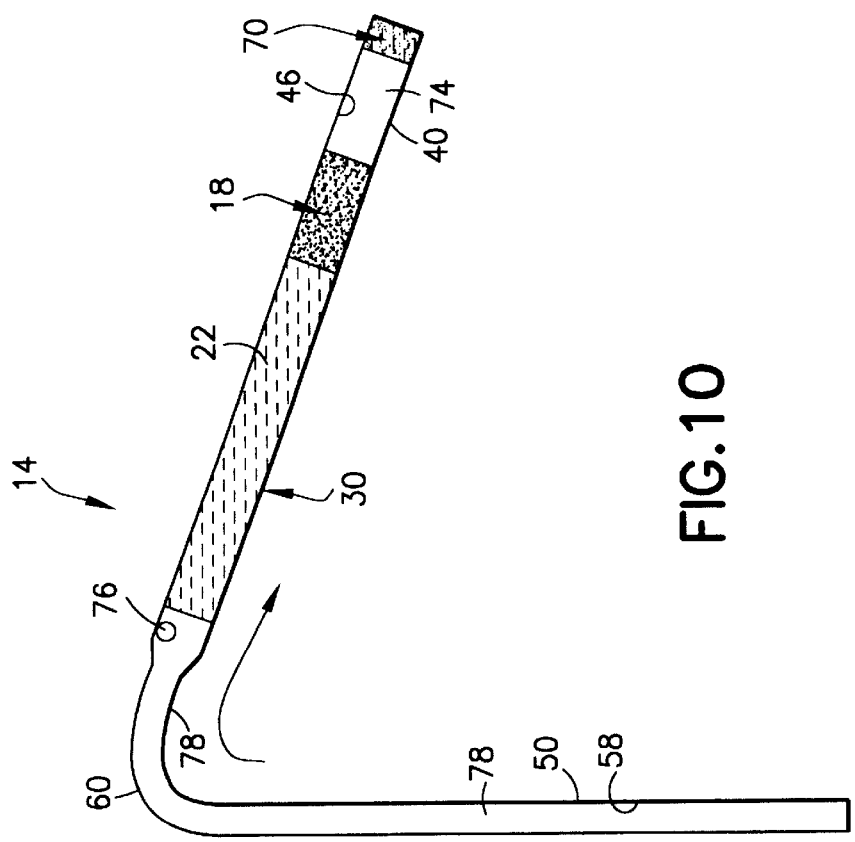
FIG. 10 is a view similar to FIG. 9, and in sequence with FIG. 9, after the aspirated test sample, the micro-bubble of air, and the diluent have been drawn into the mixing chamber of the probe.

Referring to FIG. 10 the probe 50 then aspirates a sufficient amount of trailing air 78 to draw the test sample 18, the air bubble 76 and the diluent 22 into the mixing chamber 46 of the mixing section 40. The air bubble 76 which was located between the test sample 18 and the diluent 22 can thus separate from the test sample 18 and the diluent 22 because of the downward angle of the mixing chamber 40 and the larger diameter of the mixing chamber 40 than that of the probe 50.

Although not shown, it should be noted that a coating of hydraulic fluid 70 remains on the interior wall surface of the entire hydraulic line 30 including the probe 50, the curved section 60 and the mixing chamber 40 during all stages of the aspiration and mixing process.

Once the air bubble 76 separates from the test sample 18 and the diluent 22, it can migrate to the highest point of the mixing chamber 46 as schematically indicated in FIG. 10. The air bubble 76 can then unite with the trailing air 78 that fills the probe 50, the transition section 60 and an upstream end portion of the mixing chamber 40.

Referring to FIGS. 4, 11 and 12 the pump 34 moves the now combined test sample 18 and the diluent 22 back and forth in the mixing chamber 40 approximately 2 to 20 times by alternate application of pressure and vacuum forces on the fluid in the mixing chamber 40. Preferably the stroke length for the back and forth movement of the combined test sample 18 and the diluent 22 is at least 2 times the length of the test sample 18 and the diluent 22 in the mixing section 40.

Thorough mixing of the test sample 18 and the diluent 22 is accomplished by moving the combined test sample 18 and the diluent 22 back and forth in the mixing section 40 approximately 2 to 20 times without any mixing element. The mixing rate can be approximately one reciprocation per 0.3 seconds.

Figure 13:
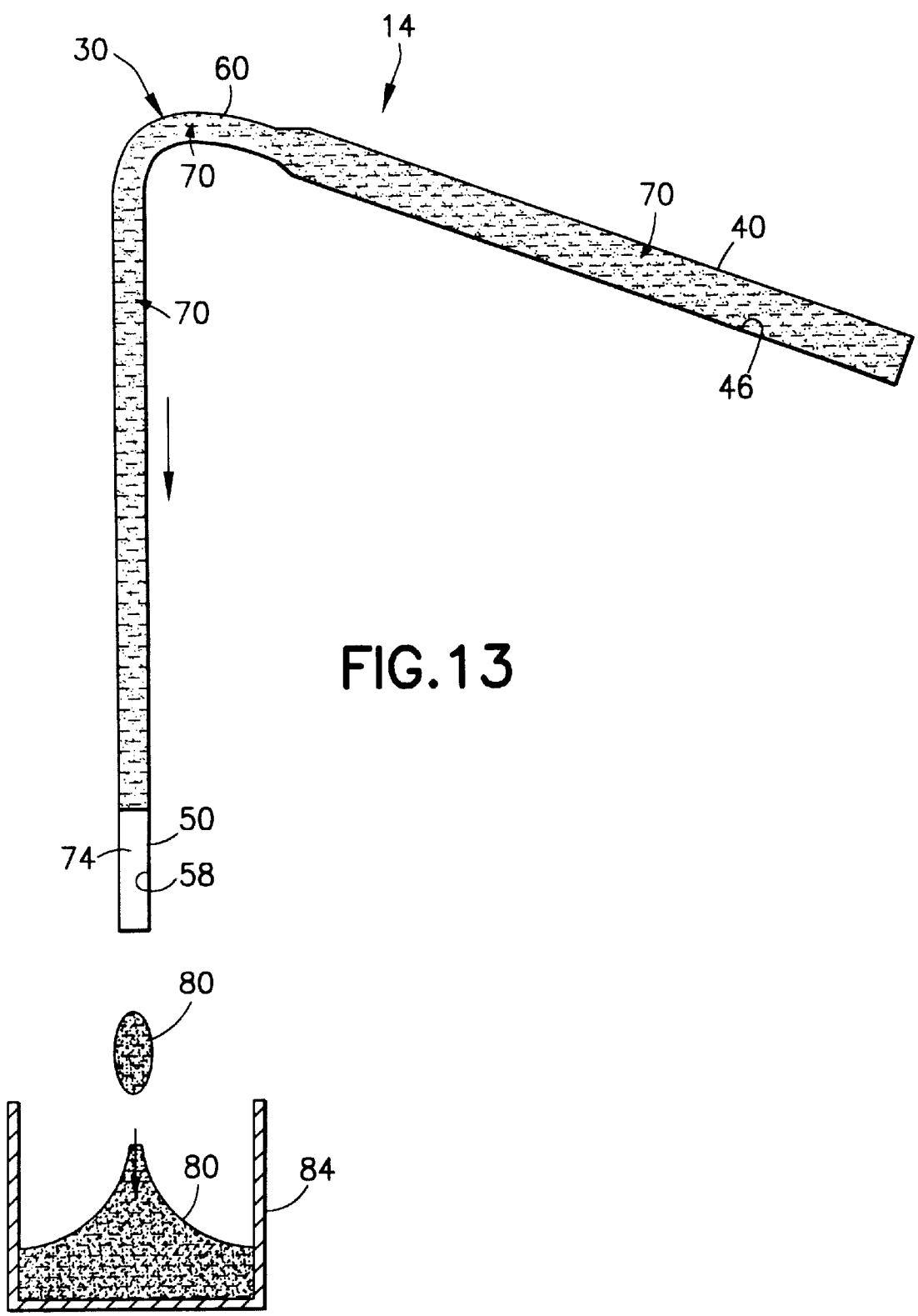

Referring to FIG. 13 the resulting homogenized mixture of the test sample 18 and the diluent 22 referred to as the diluted test sample 80, is now ready for dispensation.

If desired, the diluted test sample 80 can be dispensed into a holding container 84, for later aspiration by a probe in the sample analysis system (not shown).

It should be noted that the diluted test sample 80 is dispensed from the probe 50 free of any air from the air bubble 76 since the air bubble 76 combines with the trailing air 78 in the probe 50 and at the upstream end of the mixing section 40. The trailing air 78 is flushed out of the probe 50 in advance of the dispensed diluted test sample 80.

Some advantages of the invention evident from the foregoing description include a novel method and apparatus for diluting a test sample, a novel method and apparatus for diluting a test sample wherein the test sample and diluent are separated by an air bubble during the aspiration process and are mixed together without inclusion of the air bubble in the mixture. A further advantage is that the process and apparatus provides for mixing of the test sample and diluent along an axis that is inclined below the horizontal axis by approximately 5 to 45 degrees. This orientation helps to minimize carryover to less than five parts per million. A further advantage of the present invention is that it provides for accurately measurable dispensation volumes that do not include air mixed therein.

In view of the above, it will be seen that the several objects of the invention are achieved and other advantageous results attained.

As various changes can be made in the above constructions and method without departing from the scope of the invention, it is intended that all matter contained in the above description or shown in the accompanying drawings shall be interpreted as illustrative and not in a limiting sense.

What is claimed is:

1. A method of diluting a test sample for analysis in a sample analysis system comprising,
    (a) aspirating a first predetermined amount of test sample into an aspiration probe along a substantially vertical aspiration path,
    (b) aspirating a second predetermined amount of diluent into the aspiration probe along the substantially vertical aspiration path,
    (c) drawing the test sample and the diluent away from the vertical aspiration path into a substantially horizontal mixing chamber that is communicable with the vertical aspiration path and is without any mixing element, and,
    (d) alternately exerting suction and pressure forces on the test sample and diluent in the substantially horizontal mixing chamber to move the test sample and diluent back and forth along a substantially horizontal path in the substantially horizontal mixing chamber a predetermined number of times without agitation of the substantially horizontal mixing chamber such that the suction and pressure induced back and forth movement of the test sample and the diluent in the substantially horizontal mixing chamber provides substantially uniform mixing of the test sample and the diluent in the substantially horizontal mixing chamber, resulting in a diluted test sample,
    including forming the mixing chamber with a larger diameter than the diameter of the vertical aspiration path and inclining the mixing chamber at an angle in the range of approximately 5 to 45 degrees below a horizontal axis.

2. The method of claim 1 where the mixing chamber is inclined approximately 15 degrees below the horizontal axis.

3. The method of claim 1 including filling the aspiration probe and the mixing chamber with oil such that the oil remains in the vertical aspiration path and in the mixing chamber before the first predetermined amount of test sample is aspirated.

4. The method of claim 3 including aspirating a first predetermined volume of air into the probe before the test sample is aspirated to separate the oil in the probe and the mixing chamber from a subsequent aspiration of test sample to minimize carryover and to ensure that the entire mixture of diluted test sample can be dispensed from the aspiration probe upon reverse movement of the oil in the probe and the mixing chamber toward the tip of the probe.

5. The method of claim 4 including aspirating the first predetermined amount of test sample into the probe following the aspiration of the first predetermined volume of air.

6. The method of claim 5 including aspirating a bubble of air of predetermined volume after the test sample is aspirated and before the diluent is aspirated to separate the test sample and the diluent in the vertical aspiration path, prevent premature mixing of the test sample and the diluent, prevent loss of test sample during probe motion after the test sample is aspirated, prevent loss of test sample into the diluent while the probe is in a diluent vessel, and thus prevent test sample contamination of diluent in the diluent vessel.

7. The method of claim 6 including aspirating the second predetermined amount of diluent following the aspiration of the bubble of air, in accordance with a selected ratio of sample to diluent such that the total volume of sample and diluent does not exceed a desired total volume of diluted test sample.

8. The method of claim 7 including drawing the test sample, the diluent and the bubble of air into the mixing chamber to enable the bubble of air to separate from the test sample and the diluent in the mixing chamber.

9. The method of claim 1 including moving the test sample and the diluent in the mixing chamber back and forth approximately 2 to 20 times to accomplish mixing of the test sample and the diluent.

10. The method of claim 1 including forming the aspiration probe and the mixing chamber as a one piece structure.

11. The method of claim 10 wherein the aspiration probe is formed of perfluoropolymer material and the probe and mixing chamber are filled with fluorocarbon oil before the predetermined amount of test sample is aspirated.

12. A method of diluting a test sample for analysis in a sample analysis system comprising,
   (a) aspirating a first predetermined amount of test sample into an aspiration probe along a substantially vertical aspiration path,
   (b) aspirating a second predetermined amount of diluent into the aspiration probe along the substantially vertical aspiration path,
   (c) drawing the test sample and the diluent away from the vertical aspiration path into a substantially horizontal mixing chamber that is communicable with the vertical aspiration path and is without any mixing element, and,
   (d) alternately exerting suction and pressure forces on the test sample and diluent in the mixing chamber to move the test sample and diluent back and forth in the mixing chamber a predetermined number of times without agitation of the mixing chamber such that the suction and pressure induced back and forth movement of the test sample and the diluent in the mixing chamber provides substantially uniform mixing of the test sample and the diluent in the mixing chamber, resulting in a diluted test sample,
   wherein an air bubble of predetermined size is aspirated after the test sample is aspirated and before the diluent is aspirated to separate the test sample and the diluent in the vertical aspiration path, prevent premature mixing of the test sample and diluent, prevent loss of test sample during probe motion after the test sample is aspirated, prevent loss of sample into the diluent while the probe is in a diluent vessel, and thus prevent test sample contamination of diluent in the diluent vessel,
   including forming the mixing chamber with a diameter larger than the diameter of the vertical aspiration path and with a chamber volume greater than the volume of the test sample and diluent, and inclining the mixing chamber at an angle in the range of approximately 5 to 45 degrees below a horizontal axis such that the air bubble can separate from the test sample and diluent and remain separated during back and forth movement of the test sample and the diluent in the mixing chamber.

13. The method of claim 12 wherein the mixing chamber volume is at least 2 times greater than the combined volume of the test sample and diluent.

14. The method of claim 12 wherein the mixing chamber is inclined approximately 15 degrees below the horizontal axis.

15. A method of diluting a test sample for analysis in a sample analysis system comprising,
   (a) aspirating in sequence, selected predetermined amounts of test sample and diluent along a substantially horizontal path of an aspiration line,
   (b) moving the aspirated test sample and diluent back and forth along the substantially horizontal path of the aspiration line, without agitation and without any mixing element by alternately exerting suction and pressure forces on the test sample and diluent,
   including separating the aspirated test sample and diluent with an air bubble by aspirating the air bubble after aspirating one of the test sample and diluent and then aspirating the other of the test sample and diluent after the air bubble is aspirated, moving the test sample and diluent back and forth at an acute angle below the horizontal in a mixing chamber that is larger in cross section than the aspiration path and of greater volume than the volume of the test sample and diluent to enable the air bubble to separate from the test sample and diluent when the test sample and diluent are moved back and forth in the mixing chamber.

16. The method of claim 15 including moving the test sample and diluent back and forth at an angle of approximately 5 to 45 degrees below the horizontal.

* * * * *